(12) United States Patent
Goodenow et al.

(10) Patent No.: US 11,324,822 B2
(45) Date of Patent: May 10, 2022

(54) COMBINATION OF HDAC INHIBITOR AND ANTI-PD-1 ANTIBODY FOR TREATMENT OF CANCER

(71) Applicant: Syndax Pharmaceuticals, Inc., Waltham, MA (US)

(72) Inventors: Robert Goodenow, San Clemente, CA (US); Peter Ordentlich, Lexington, MA (US)

(73) Assignee: Syndax Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 15/559,402

(22) PCT Filed: Mar. 18, 2016

(86) PCT No.: PCT/US2016/023298
§ 371 (c)(1),
(2) Date: Sep. 18, 2017

(87) PCT Pub. No.: WO2016/154068
PCT Pub. Date: Sep. 29, 2016

(65) Prior Publication Data
US 2018/0078639 A1 Mar. 22, 2018

Related U.S. Application Data

(60) Provisional application No. 62/137,601, filed on Mar. 24, 2015, provisional application No. 62/136,303, filed on Mar. 20, 2015.

(51) Int. Cl.
| | | |
|---|---|---|
| A61K 39/395 | (2006.01) | |
| A61K 31/4406 | (2006.01) | |
| C07K 16/28 | (2006.01) | |
| A61K 39/00 | (2006.01) | |

(52) U.S. Cl.
CPC .... *A61K 39/39558* (2013.01); *A61K 31/4406* (2013.01); *A61K 39/39541* (2013.01); *C07K 16/2818* (2013.01); *A61K 2039/505* (2013.01); *A61K 2039/54* (2013.01); *A61K 2039/545* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 2013/0150386 A1 | 6/2013 | Goodenow et al. | |
| 2016/0108123 A1* | 4/2016 | Freeman | C07K 16/2827 424/85.2 |
| 2017/0049755 A1* | 2/2017 | Villagra | A61K 45/06 |
| 2017/0189526 A1* | 7/2017 | Zhou | A61K 45/06 |
| 2018/0252721 A1* | 9/2018 | Ordentlich | A61P 43/00 |
| 2018/0353602 A1* | 12/2018 | Goodenow | C12Q 1/6886 |

FOREIGN PATENT DOCUMENTS

| | | |
|---|---|---|
| WO | 2015016718 A1 | 2/2015 |
| WO | 2015035112 A1 | 3/2015 |

OTHER PUBLICATIONS

Garon, E. et al. (J. Thoracic Oncology Nov. 2013 8(Suppl. 2): S364-S365, Ab. No. MO18.02) (Year: 2013).*
Clinical Trial NCT02437136 (SNDX-275-0601, May 4, 2015, https://clinicaltrials.gov/ct2/history/NCT02437136?A=1&B=1&C=merged#StudyPageTop) (Year: 2015).*
Mahoney et al., "Prognostic and Predictive Markers for the New Immunotherapies", Oncology, Nov. 10, 2014, pp. 1-10, vol. 28, No. 3.
ESMO 2014: Results of a Phase III Randomised Study of Nivolumab in Patients with Advanced Melanoma After Prior Anti-CTLA4 Therapy, Sep. 29, 2014.
Carter, C. A. et al. "Addressing the elephant in the room, therapeutic resistance in non-small cell lung cancer, with epigenetic therapies", Oncotarget, (2016), vol. 7, No. 26, p. 40781-40791.
Forde, P. M. et al. "New strategies in lung cancer: epigenetic therapy for non-small cell lung cancer", Clinical cancer research, (2014), vol. 20, No. 9, p. 2244-2248.
Frys, S. et al. "Entinostat, a novel histone deacetylase inhibitor is active in B-cell lymphoma and enhances the anti-tumour activity of rituximab and chemotherapy agents", British journal of haematology, (2015), vol. 169, No. 4, p. 506-519.
Weintraub, K. Take two: Combining immunotherapy with epigenetic drugs to tackle cancer, Nature medicine, (2016), vol. 22, No. 1, p. 8-10.
Wrangle, J. et al. "Alterations of immune response of nonsmall cell lung cancer with Azacytidine", Oncotarget, (2013) vol. 4, No. 11, p. 2067-2079.
Azad, N. et al. "The future of epigenetic therapy in solid tumours—lessons from the past", Nature Reviews, Clinical Oncology, 2013, vol. 10, p. 256-266.
Lee et al. "Patients [Pts] with advanced NSCLC from Korea treated with pembrolizumab (Pembro) in KEYNOTE-001", Annals of Oncology, 2015, vol. 26, Issue suppl. 9, p. 461.
Gore et al. "A phase I and pharmacokinetic study of the oral histone deacetylase inhibitor, MS-275, in patients with refractory solid tumors and lymphomas", Clinical Cancer Research, vol. 14, 2008, pp. 4517-4525.
McDermott J. "Pembrolizumab: PD-1 inhibition as a therapeutic strategy in cancer", Drugs Today (Barc), vol. 51, No. 1, 2015, pp. 7-20.
Woods, D. "Abstract 4090: Inhibition of class I histone deacetylases promotes robust and durable enhancement of POLI expression in melanoma: Rationale for combination therapy", Cancer Research, vol. 74, No. 19, 2014, 1 page.

* cited by examiner

*Primary Examiner* — Peter J Reddig
(74) *Attorney, Agent, or Firm* — Cooley LLP; Heidi A. Erlacher; Eric A. Owens

(57) ABSTRACT

Described herein are methods for the treatment of cancer in a subject. In particular, methods are provided for the treatment of non small cell lung cancer and melanoma with a combination of entinostat and an anti-PD-1 or an anti-PD-L1 antibody.

24 Claims, No Drawings

COMBINATION OF HDAC INHIBITOR AND ANTI-PD-1 ANTIBODY FOR TREATMENT OF CANCER

CROSS-REFERENCE

This application is a national stage application, filed under 35 U.S.C. 371, of PCT Application No. PCT/US2016/023298, which claims the benefit of U.S. Provisional Application No. 62/136,303 filed Mar. 20, 2015, and 62/137,601 filed Mar. 24, 2015, which are incorporated by reference herein in their entirety.

SUMMARY OF THE INVENTION

Provided herein in one embodiment is a method of treating cancer, wherein the method comprises, administering to a patient a combination comprising entinostat, and an anti PD-1 or an anti-PD-L1 antibody. In some embodiments, the method comprises, administering to a patient a combination comprising entinostat, and an anti PD-1 antibody. In some embodiments, the anti PD-1 antibody is pembrolizumab. In some embodiments, the cancer is characterized by overexpression of PD-L1. In some embodiments, the cancer is characterized by low expression of PD-L1. In some embodimethe cancer is lung cancer or melanoma. In some embodiments, the patient received at least one prior therapy. In some embodiments, the prior therapy was with an anti-PD-1 antibody. In some embodiments, the cancer is lung cancer. In some embodiments, the lung cancer is a non-small cell lung cancer. In some embodiments, the non-small cell lung cancer is selected from adenocarcinoma, squamous cell carcinoma, and large cell carcinoma. In some embodiments, the cancer is melanoma. In some embodiments, the melanoma is unresectable or metastatic melanoma. In some embodiments, the patient has progressed on a prior therapy with an anti-CTLA4 antibody. In some embodiments, the patient has progressed on a prior therapy with a BRAF inhibitor. In some embodiments, the entinostat, and the anti-PD-1 or the anti-PD-L1 antibody are administered sequentially in either order or simultaneously. In some embodiments, the anti-PD-1 or the anti-PD-L1 antibody are administered sequentially in either order or simultaneously during a treatment cycle of 21 days. In some embodiments, the entinostat and the anti-PD-1 antibody are administered sequentially in either order or simultaneously. In some embodiments, the entinostat and the anti-PD-1 antibody are administered sequentially in either order or simultaneously during a treatment cycle of 21 days. In some embodiments, the anti-PD-1 antibody is administered on day 1 of the treatment cycle. In some embodiments, the anti-PD-1 antibody is administered at a dose of 2 mg/kg. In some embodiments, the anti-PD-1 antibody is administered at a fixed dose of 200 mg. In some embodiments, the entinostat is administered at a dose of 3 mg/kg. In some embodiments, the entinostat is administered at a dose of 5 mg/kg. In some embodiments, the entinostat is administered at a dose of 10 mg/kg. In some embodiments, the entinostat is administered weekly. In some embodiments, the anti-PD-1 antibody or the anti-PD-L1 antibody is administered every two weeks.

Provided herein in a further embodiment is a method of treating a cancer, wherein the method comprises, administering to a patient a combination consisting essentially of entinostat and pembrolizumab. In some embodiments, the entinostat is administered as a solid dosage form and the pembrolizumab is administered as intravenous infusion. In some embodiments, the cancer is lung cancer or melanoma.

Provided herein in another embodiment is a kit for treating advanced non-small cell lung cancer and melanoma comprising a combination of entinostat, and an anti-PD-1 or an anti-PD-L1 antibody.

Provided herein in another embodiment is a method of selecting a patient for a combination therapy comprising administering entinostat, and an anti-PD-1 or an anti-PD-L1 antibody, the method comprising measuring PD-L1 expression in a tumor tissue sample obtained from the patient.

In some embodiments, the method further comprises administering to the patient the combination therapy comprising entinostat, and an anti-PD-1 or an anti-PD-L1 antibody if tumor proportion score (TPS) for PD-L1 expression is greater than or equal to 50%. In some embodiments, the method further comprises administering to the patient the combination therapy comprising entinostat, and an anti-PD-1 or an anti-PD-L1 antibody if tumor proportion score (TPS) for PD-L1 expression is greater than or equal to 1%. In some embodiments, the method further comprises administering to the patient the combination therapy comprising entinostat, and an anti-PD-1 or an anti-PD-L1 antibody if tumor proportion score (TPS) for PD-L1 expression is between 1% and 50%. In some embodiments, the method further comprises administering to the patient the combination therapy comprising entinostat, and an anti-PD-1 or an anti-PD-L1 antibody if tumor proportion score (TPS) for PD-L1 expression is greater than or equal to 49%. In some embodiments, the tumor tissue sample is from a squamous or nonsqaumos non small cell lung cancer. In some embodiments, the tumor tissue sample is from a melanoma.

INCORPORATION BY REFERENCE

All publications, patents, and patent applications described in this specification are herein incorporated by reference to the same extent as if each individual publication, patent, or patent application was specifically and individually indicated to be incorporated by reference.

DETAILED DESCRIPTION

Novel strategies are needed for cancer therapy, in particular unresectable or metastatic melanoma, and non small cell lung cancer, which do not have satisfactory progress when treated with currently known methods. Combination therapy using epigenetic modulation with histone deacetylase (HDAC) inhibitors, such as entinostat, and immune-checkpoint inhibitors, such as anti-PD-1 or anti-PD-L1 antibodies have been surprisingly found to provide effective strategy for treatment of cancer, in particular melanoma and non small cell lung cancer.

Provided herein are methods of treating cancer based on the administration of an HDAC inhibitor, and an anti PD-1 antibody or an anti-PD-L1 antibody. In some embodiments, the HDAC inhibitor is entinostat. In some embodiments, the anti PD-1 antibody is pembrolizumab. The methods may further include treatments wherein the combination is supplemented with one or more therapeutic agents or therapies.

To facilitate understanding of the disclosure set forth herein, a number of terms are defined below.

As used herein, "abnormal cell growth," refers to cell growth that is independent of normal regulatory mechanisms (e.g., loss of contact inhibition), including the abnormal growth of normal cells and the growth of abnormal cells.

"Neoplasia" as described herein, is an abnormal, unregulated and disorganized proliferation of cells that is distinguished from normal cells by autonomous growth and somatic mutations. As neoplastic cells grow and divide they pass on their genetic mutations and proliferative characteristics to progeny cells. A neoplasm, or tumor, is an accumulation of neoplastic cells. In some embodiments, the neoplasm can be benign or malignant.

"Metastasis," as used herein, refers to the dissemination of tumor cells via lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

As discussed herein, "angiogenesis" is prominent in tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors such as renal cell carcinoma, hepatocellular carcinoma, and benign tumors such as acoustic neuroma, and neurofibroma. Angiogenesis has been associated with blood-born tumors such as leukemias. It is believed that angiogenesis plays a role in the abnormalities in the bone marrow that give rise to leukemia. Prevention of angiogenesis could halt the growth of cancerous tumors and the resultant damage to the subject due to the presence of the tumor.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition; or one or more of the symptoms associated with the disorder, disease, or condition; or alleviating or eradicating the cause(s) of the disorder, disease, or condition itself.

The term "therapeutically effective amount" refers to the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

Cancer, tumors, tumor-related disorders, and neoplastic disease states are serious and often times life-threatening conditions. These diseases and disorders, which are characterized by rapidly-proliferating cell growth, continue to be the subject of research efforts directed toward the identification of therapeutic agents which are effective in the treatment thereof. Such agents prolong the survival of the patient, inhibit the rapidly-proliferating cell growth associated with the neoplasm, or effect a regression of the neoplasm.

HDAC inhibitors are an emerging class of therapeutic agents that promote differentiation and apoptosis in hematologic and solid malignancies through chromatin remodeling and gene expression regulation. Several HDAC inhibitors have been identified including benzamides (entinostat), short-chain fatty acids (i.e., Sodium phenylbutyrate); hydroxamic acids (i.e., suberoylanilide hydroxamic acid and thrichostatin A); cyclic tetrapeptides containing a 2-amino-8-oxo-9, 10-epoxy-decanoyl moiety (i.e., trapoxin A) and cyclic peptides without the 2-amino-8-oxo-9, 10-epoxy-decanoyl moiety (i.e., FK228). Entinostat is a benzamide HDAC inhibitor undergoing clinical investigation in multiple types of solid tumors and hematologic cancers. Entinostat is rapidly absorbed and has a half-life of about 100 hours and, importantly, changes in histone acetylation persist for several weeks following the administration of entinostat.

High expression of PD-L1 on tumor cells has been found to correlate with poor prognosis and survival in various other solid tumor types. Without being bound by any theory it is contemplated that the PD-1/PD-L1 pathway plays a critical role in the tumor immune evasion and could be considered an attractive target for therapeutic intervention in several solid organ types.

Several PD-1 and PD-L1 antibodies are in clinical development. Overall, they have been reported to be well tolerated, with most not reaching dose-limiting toxicity in their phase I studies.

Histone Deacetylase

The HDACs are a family including at least eighteen enzymes, grouped in three classes (Class I, II and III). Class I HDACs include, but are not limited to, HADCs 1, 2, 3, and 8. Class I HDACs can be found in the nucleus and are believed to be involved with transcriptional control repressors. Class II HDACs include, but are not limited to, HDACS 4, 5, 6, 7, and 9 and can be found in both the cytoplasm as well as the nucleus. Class III HDACs are believed to be NAD dependent proteins and include, but are not limited to, members of the Sirtuin family of proteins. Non-limiting examples of sirtuin proteins include SIRT1-7.

As used herein, the term "selective HDAC" refers to an HDAC inhibitor that does not interact with all three HDAC classes.

HDAC Inhibitors

HDAC inhibitors can be classified broadly into pan HDAC inhibitors and selective HDAC inhibitors. Although there is a large structural diversity of known HDAC inhibitors, they share common features: a part that interacts with the enzyme active site and a side-chain that sits inside the channel leading to the active site. This can be seen with the hydroxamates such as SAHA, where the hydroxamate group is believed to interact with the active site. In the case of the depsipeptides, it is believed that an intracellular reduction of the disulphide bond creates a free thiol group (which interacts with the active site) attached to a 4-carbon alkenyl chain. A difference between the HDAC inhibitors is in the way that they interact with the rim of the HDAC channel, which is at the opposite end of the channel to the active site. It is this interaction, between the HDAC inhibitor and the rim of the channel, which is believed to account, at least in part, for some observed differences in HDAC selectivity between pan-HDAC inhibitors, such as SAHA and selective HDAC inhibitors such as the depsipeptides. A particularly preferred HDAC inhibitor is entinostat. Entinostat has the chemical name N-(2-aminophenyl)-4-[N-(pyridine-3-yl) methoxycarbonylamino-methyl]-benzamide and the chemical structure shown below.

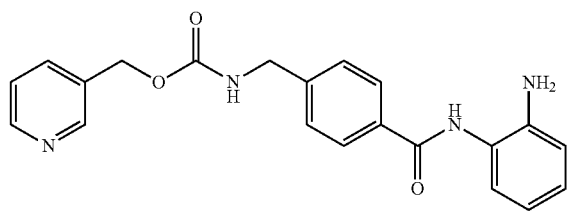

Chemical structure of entinostat

Programmed Cell Death-1 (PD-1)

PD-1 is a cell surface receptor that is a member of the CD28 family of T-cell regulators, within the immunoglobulin superfamily of receptors. The human PD-1 gene is located at chromosome 2q37, and the full-length PD-1 cDNA encodes a protein with 288 amino acid residues with 60% homology to murine PD-1. It is present on CD4 CD8 (double negative) thymocytes during thymic development and is expressed upon activation in mature hematopoietic cells such as T and B cells, NKT cells and monocytes after prolonged antigen exposure.

PD-L1 has been shown to be expressed on a number of mouse and human tumors (and is inducible by IFN gamma on the majority of PD-L1 negative tumor cell lines) and is postulated to mediate immune evasion (Iwai Y. et al., Proc. Natl. Acad. Sci. U.S.A. 99: 12293-12297 (2002); Strome S. E. et al., Cancer Res., 63: 6501-6505 (2003). In humans, expression of PD-1 and/or PD-L1 has been found in a number of primary tumor biopsies from cancers of the lung, liver, ovary, cervix, skin, colon, glioma, bladder, breast, kidney, esophagus, stomach, oral squamous cell, urothelial cell, and pancreas as well as tumors of the head and neck (Brown J. A. et al., J. Immunol. 170: 1257-1266 (2003); Dong H. et al., Nat. Med. 8: 793-800 (2002); Wintterle et al., Cancer Res. 63: 7462-7467 (2003); Strome S. E. et al., Cancer Res., 63: 6501-6505 (2003); Thompson R. H. et al., Cancer Res. 66: 3381-5 (2006); Thompson et al., Clin. Cancer Res. 13: 1757-61 (2007); Nomi T. et al., Clin. Cancer Res. 13: 2151-7. (2007)). PD-ligand expression on tumor cells has been correlated to poor prognosis of cancer patients across multiple tumor types (reviewed in Okazaki and Honjo, Int. Immunol. 19: 813-824 (2007)).

Several studies have shown that interaction of PD-1 with its ligands (PD-L1 and PD-L2) leads to the inhibition of lymphocyte proliferation in vitro and in vivo. Accordingly, without being bound by any theory, it is contemplated that binding of the ligand PD-L1 to PD-1 downregulates effector anti-tumor T-cell activity and facilitates immune evasion.

Disruption of the PD-1/PD-L1 interaction has been shown to increase T cell proliferation and cytokine production and block progression of the cell cycle. In vitro studies of PD-1 blockade by PD-1-specific antibody showed augmentation of cytotoxic T-cell responses to melanoma-specific antigens including increased frequencies of IFN-γ-secreting antigen-specific cells.

Without being bound by any theory, it is contemplated that targeting PD-1 may act as an effective therapeutic strategy for cancer.

The principal method for targeting PD-1 clinically has been through the development of genetically engineered monoclonal antibodies that inhibit either PD-1 or PD-L1 function.

The methods of the present disclosure include use of full-length antibodies against PD-1 (anti-PD-1 antibody) and antigen binding portion thereof. Examples of binding fragments encompassed within the term "antigen-binding portion thereof" include (i) a Fab fragment, a monovalent fragment consisting of the Vi, V//, CL and C domains; (ii) a F(ab')2 fragment, a bivalent fragment comprising two Fab fragments linked by a disulfide bridge at the hinge region; (iii) a Fd fragment consisting of the \1H and Cm domains; and (iv) a Fv fragment consisting of the Vi and V// domains of a single arm of an Ab.

The anti-PD-1 antibody and antigen binding portion thereof, bind to PD-1 with high specificity and affinity, block the binding of PD-L1 and or PD-L2, and inhibit the immunosuppressive effect of the PD-1 signaling pathway. In some embodiments, the combination therapy comprises administering entinostat and, an anti-PD-1 antibody or antigen-binding portion thereof, wherein the antibody or antigen-binding portion thereof is a chimeric, humanized or human monoclonal antibody or a portion thereof. In certain embodiments, the anti-PD-1 antibody or antigen-binding portion thereof is a humanized antibody. In some embodiments, the anti-PD-1 antibody or antigen-binding portion thereof is a human antibody. In some embodiments, the anti-PD-1 antibody or antigen-binding portion thereof is a monoclonal antibody or an antigen-binding portion thereof.

Without being bound by any theory it is contemplated that an anti-PD-L1 antibody prevents interaction between PD-1 and PD-L1, thereby exerting similar effects to the signaling pathway of PD-1. Accordingly, in some embodiments the combination therapy comprises administering entinostat, and an anti-PD-L1 antibody. In some embodiments, the anti-PD-L1 antibody or an antigen-binding portion thereof binds specifically to a Programmed Death-Ligand 1 (PD-L1) receptor and inhibits PD-L1 activity.

Pembrolizumab

Pembrolizumab is a humanized monoclonal IgG4 anti-PD-1 antibody consisting of a high-affinity mouse anti-PD-1-derived variable region grafted on to a human IgG4 immunoglobulin molecule with an engineered Fc region for stabilization. Pembrolizumab has been approved by the FDA for the treatment of unresectable or metastatic melanoma and metastatic non small cell lung cancer (NSCLC).

Lung Cancer

Lung cancer is the leading cause of cancer deaths in women and men both in the United States and throughout the world. Lung cancer has surpassed breast cancer as the leading cause of cancer deaths in women. In the United States in 2014, 158,040 people were projected to die from lung cancer, which is more than the number of deaths from colon and rectal, breast, and prostate cancer combined. Only about 2% of those diagnosed with lung cancer that has spread to other areas of the body are alive five years after the diagnosis, although the survival rates for lung cancers diagnosed at the earliest stage are higher, with approximately 49% surviving for five years or longer.

Cancer occurs when normal cells undergo a transformation that causes them to grow and multiply without control. The cells form a mass or tumor that differs from the surrounding tissues from which it arises. Tumors are dangerous because they take oxygen, nutrients, and space from healthy cells and because they invade and destroy or reduce the ability of normal tissues to function.

Most lung tumors are malignant. This means that they invade and destroy the healthy tissues around them and can spread throughout the body. The tumors can spread to nearby lymph nodes or through the bloodstream to other organs. This process is called metastasis. When lung cancer metastasizes, the tumor in the lung is called the primary tumor, and the tumors in other parts of the body are called secondary tumors or metastatic tumors.

Some tumors in the lung are metastatic from cancers elsewhere in the body. The lungs are a common site for metastasis. If this is the case, the cancer is not considered to be lung cancer. For example, if prostate cancer spreads via the bloodstream to the lungs, it is metastatic prostate cancer (a secondary cancer) in the lung and is not called lung cancer.

Lung cancer comprises a group of different types of tumors. Lung cancers usually are divided into two main groups that account for about 95% of all cases. The division into groups is based on the type of cells that make up the cancer. The two main types of lung cancer are characterized by the cell size of the tumor when viewed under the microscope. They are called small cell lung cancer (SCLC) and non-small cell lung cancer (NSCLC). NSCLC includes several subtypes of tumors. SCLCs are less common, but they grow more quickly and are more likely to metastasize than NSCLCs. Often, SCLCs have already spread to other parts of the body when the cancer is diagnosed. About 5% of lung cancers are of rare cell types, including carcinoid tumor, lymphoma, and others. As used herein, the term "lung cancer" includes, but is not limited to, SCLC, NSCLC, carcinoid tumor, lymphoma, and their various subtypes.

Non-Small Cell Lung Cancer

NSCLC is a cancer of the lung which is not of the small cell carcinoma (oat cell carcinoma) type. The term "non-small cell lung cancer" applies to the various types of bronchogenic carcinomas (those arising from the lining of the bronchi). Examples of specific types of NSCLC include, but are not limited to, non-squamous cell carcinoma, such as adenocarcinoma, large cell cancer (i.e., large cell undifferentiated carcinoma), and squamous cell carcinoma.

Adenocarcinoma is a cancer that develops in the lining or inner surface of an organ. Adenocarcinoma is the most common type of lung cancer, making up 30%-40% of all cases of lung cancer. A subtype of adenocarcinoma is called bronchoalveolar cell carcinoma, which creates a pneumonia-like appearance on chest X-rays.

Squamous cell carcinoma is a cancer that begins in squamous cells. Squamous cells are thin, flat cells that look under the microscope like fish scales. Squamous cells are found in the tissue that forms the surface of the skin, the lining of hollow organs of the body, and the passages of the respiratory and digestive tracts. Squamous cell carcinomas may arise in any of these tissues. Squamous cell carcinoma is the second most common type of lung cancer, making up about 30% of all cases.

Large cell carcinoma shows no evidence of squamous or glandular maturation. Thus these tumors are often diagnosed by default, when all other possibilities have been excluded. These tumors lack any diagnostic features to suggest their diagnosis prior to biopsy. They tend to grow rapidly, metastasize early, and are strongly associated with smoking. Large cell tumors are usually large, bulky, well-circumscribed, pink-grey masses with extensive hemorrhage and necrosis. Although they commonly have central necrosis, they rarely cavitate. They tend to present in the mid to peripheral lung zones. They may extend locally to involve the segmental or subsegmental bronchi. A variant of large cell carcinoma is giant cell carcinoma. This subtype is particularly aggressive and carries a very poor prognosis. These tumors generally present as a large peripheral mass with a focal necrotic component. They do not involve the large airways, unless by direct extension. Large cell cancer makes up 10%-20% of all cases of lung cancer.

In some embodiments, the method described herein comprises administering to a NSCLC patient a combination therapy comprising entinostat, and an anti PD-1 or an anti-PD-L1 antibody, wherein said patient expresses elevated levels of PD-L1 in a squamous or nonquamous tumor tissue sample. In some embodiments, the method described herein comprises administering to a NSCLC patient a combination therapy comprising entinostat, and an anti PD-1 or an anti-PD-L1 antibody, wherein said patient has a PD-L1 tumor proportion score (PD-L1 TPS) between 1% and 50% in a squamous or a nonquamous tumor tissue sample. In some embodiments, the method described herein comprises administering to a NSCLC patient a combination therapy comprising entinostat, and an anti PD-1 or an anti-PD-L1 antibody, wherein said patient has a PD-L1 tumor proportion score (PD-L1 TPS) of 50% or greater in a squamous or nonquamous tumor tissue sample. PD-L1 TPS is a measure of the percentage of cells in a tumor tissue sample that stains positive for PD-L1 expression, as determined using immunohistochemistry. In some embodiments, PD-L1 TPS is determined using a PD-L1 IHC 22C3 pharmDx kit.

Melanoma

Melanoma is a malignant tumor of melanocytes, which are the cells that make the pigment melanin and are derived from the neural crest. Although most melanomas arise in the skin, they may also arise from mucosal surfaces or at other sites to which neural crest cells migrate, including the uveal tract. Uveal melanomas differ significantly from cutaneous melanoma in incidence, prognostic factors, molecular characteristics, and treatment.

In the United States in 2014, 9,710 people were projected to die from melanoma, and numbers of new cases were estimated to be 76,100. Skin cancer is the most common malignancy diagnosed in the United States, with 3.5 million cancers diagnosed in 2 million people annually. Melanoma represents less than 5% of skin cancers but results in most deaths. The incidence has been increasing over the past four decades. Elderly men are at highest risk; however, melanoma is the most common cancer in young adults aged 25 to 29 years and the second most common cancer in those aged 15 to 29 years. Ocular melanoma is the most common cancer of the eye, with approximately 2,000 cases diagnosed annually.

Melanoma occurs predominantly in adults, and more than 50% of the cases arise in apparently normal areas of the skin. Although melanoma can occur anywhere, including on mucosal surfaces and the uvea, melanoma in women occurs more commonly on the extremities, and in men it occurs most commonly on the trunk or head and neck.

Prognosis of melanoma is affected by the characteristics of primary and metastatic tumors. The most important prognostic factors include, but are not limited to, the following: Thickness and/or level of invasion of the melanoma, Mitotic index, defined as mitoses per millimeter, Ulceration or bleeding at the primary site, Number of regional lymph nodes involved, with distinction of macrometastasis and micrometastasis, Systemic metastasis, Site—nonvisceral versus lung versus all other visceral sites, Elevated serum lactate dehydrogenase level. Without being bound by any theory, it is contemplated that the presence of tumor infiltrating lymphocytes can be a potential prognostic factor. PD-1 has been reported to be predominantly expressed by tumor infiltrating T lymphocytes, in melanoma.

Methods for the Treatment of Non Small Cell Lung Cancer and Melanoma

One embodiment provides a method of treating cancer in a patient, wherein the method comprises, administering to the patient a combination comprising entinostat, and an anti PD-1 or an anti-PD-L1 antibody. Another embodiment provides the method of treating cancer in a patient, wherein the method comprises, administering to the patient a combination comprising entinostat, and an anti PD-1 antibody. Another embodiment provides the method, wherein the anti PD-1 antibody is pembrolizumab.

Another embodiment provides the method, wherein the cancer wherein the cancer is characterized by overexpression of PD-L1. Another embodiment provides the method, wherein the wherein the cancer is characterized by low expression of PD-L1. Another embodiment provides the method, wherein the cancer is lung cancer or melanoma. Another embodiment provides the method, wherein the cancer is lung cancer. Another embodiment provides the method, wherein the lung cancer is non-small cell lung cancer. Another embodiment provides the method, wherein the non-small cell lung cancer is adenocarcinoma. Another embodiment provides the method, wherein the non-small cell lung cancer is squamous cell carcinoma. Another embodiment provides the method, wherein the non-small cell lung cancer is large cell carcinoma. Another embodiment provides the method, wherein the cancer is melanoma.

Another embodiment provides the method, wherein the patient received at least one prior therapy. Another embodiment provides the method, wherein the prior therapy is for treatment of cancer. Another embodiment provides the method, wherein the cancer is locally advanced. Another embodiment provides the method, wherein the cancer is metastatic. Another embodiment provides the method, wherein the prior therapy was with an anti-PD-1 antibody Another embodiment provides the method, wherein the entinostat and anti-PD-1 or anti-PD-L1 antibody are administered sequentially in either order or simultaneously. Another embodiment provides the method, wherein the entinostat and anti-PD-1 antibody are administered sequentially in either order or simultaneously. Another embodiment provides the method, wherein the entinostat and anti-PD-1 antibody are administered sequentially in either order or simultaneously, during a treatment cycle of 21 days. Another embodiment provides the method, wherein the anti-PD-1 antibody is administered on day 1 of the treatment cycle. Another embodiment provides the method, wherein the anti-PD-1 antibody is administered at a dose of 0.1 to 10 mg/kg. Another embodiment provides the method, wherein the anti-PD-1 antibody is administered at a dose of 2 mg/kg. Another embodiment provides the method, wherein the anti-PD-1 antibody is administered as intravenous infusion. Another embodiment provides the method, wherein the anti-PD-1 antibody is administered as intravenous infusion over a period of 15 mins to 60 mins. Another embodiment provides the method, wherein the anti-PD-1 antibody is administered at a dose of 2 mg/kg as intravenous infusion over a period of 15 mins to 60 mins. Another embodiment provides the method, wherein the anti-PD-1 antibody is administered at a dose of 2 mg/kg as intravenous infusion over a period of 30 mins. Another embodiment provides the method, wherein the anti-PD-1 antibody is administered at a dose of 2 mg/kg as intravenous infusion over a period of 15 mins to 60 mins once every 2 weeks. Another embodiment provides the method, wherein the anti-PD-1 antibody is administered at a dose of 2 mg/kg as intravenous infusion over a period of 15 mins to 60 mins once every 3 weeks. Another embodiment provides the method, wherein the anti-PD-1 antibody is administered at a dose of 2 mg/kg as intravenous infusion over a period of 15 mins to 60 mins once every 4 weeks. Another embodiment provides the method, wherein the anti-PD-1 antibody is administered at fixed dose of 200 mg. Another embodiment provides the method, wherein the anti-PD-1 antibody is administered at fixed dose of 200 mg, every 3 weeks, via intravenous infusion. Another embodiment provides the method, wherein the entinostat is administered periodically during the treatment cycle. Another embodiment provides the method, wherein the entinostat is administered on day 1 of the treatment cycle. Another embodiment provides the method, wherein the entinostat is administered on day 8 of the treatment cycle. Another embodiment provides the method, wherein the entinostat is administered on day 15 of the treatment cycle. Another embodiment provides the method, wherein the entinostat is administered at a dose of 3 mg/kg. Another embodiment provides the method, wherein the entinostat is administered at a dose of 5 mg/kg. Another embodiment provides the method, wherein the entinostat is administered at a dose of 10 mg/kg. Another embodiment provides the method, wherein entinostat is administered first. Another embodiment provides the method, wherein entinostat is administered periodically. Another embodiment provides the method, wherein entinostat is administered weekly. Another embodiment provides the method, wherein entinostat is administered every two weeks. Another embodiment provides the method, wherein the entinostat is administered every two weeks, at a dose of 10 mg/kg. Another embodiment provides the method, wherein entinostat and anti-PD-1 or anti-PD-L1 antibody are administered simultaneously. Another embodiment provides the method, wherein entinostat and anti-PD-1 antibody are administered simultaneously.

In some embodiments are provided methods of treating cancer in a patient, comprising administering to the patient a combination comprising entinostat, and an anti PD-1 or an anti-PD-L1 antibody, wherein the combination does not comprise any additional therapeutic agent. In some embodiments are provided methods of treating cancer in a patient, comprising administering to the patient a combination comprising entinostat, and an anti PD-1 or an anti-PD-L1 antibody, wherein the combination does not comprise any additional immunecheckpoint inhibitor. In some embodiments are provided methods of treating cancer in a patient, comprising administering to the patient a combination comprising entinostat, and an anti PD-1 or an anti-PD-L1 antibody, wherein the combination does not comprise an anti-CTLA4 inhibitor. In some embodiments are provided methods of treating cancer in a patient, comprising administering to the patient a combination comprising entinostat, and an anti PD-1 or an anti-PD-L1 antibody, wherein the combination does not comprise 5-azacytidine.

In one embodiment is provided a method of treating cancer in a patient, comprising administering to the patient a combination consisting essentially of entinostat, and an anti PD-1 or an anti-PD-L1 antibody. In some embodiments are provided methods of treating cancer in a patient, comprising administering to the patient a combination consisting essentially of entinostat, and an anti PD-1 or an anti-PD-L1 antibody, wherein the entinostat is provided in a solid dosage form. In some embodiments are provided methods of treating cancer in a patient, comprising administering to the patient a combination consisting essentially of entinostat and an anti PD-1 or an anti-PD-L1 antibody, wherein the anti-PD-1 antibody or the anti-PD-L1 antibody is provided in the form of intraveous infusion. In some embodiments are provided methods of treating cancer in a patient, comprising administering to the patient a combination consisting essentially of entinostat and an anti PD-1 or an anti-PD-L1 antibody, wherein the entinostat is provided in a solid dosage form and the anti-PD-1 antibody or the anti-PD-L1 antibody is provided in the form of intraveous infusion. In some embodiments are provided methods of treating cancer in a patient, comprising administering to the patient a combination consisting essentially of entinostat, and an anti PD-1 or an anti-PD-L1 antibody, wherein the entinostat is provided in a solid dosage form and the anti-PD-1 antibody antibody is provided in the form of intraveous infusion. In some embodiments are provided methods of treating cancer in a patient, comprising administering to the patient a combination consisting essentially of entinostat and pembrolizumab, wherein the entinostat is provided in a solid dosage form and pembrolizumab is provided in the form of intraveous infusion.

In one embodiment is provided a method of treating cancer in a patient, comprising administering to the patient a combination consisting essentially of entinostat, and an anti PD-1 or an anti-PD-L1 antibody, wherein the combination does not comprise any additional therapeutic agent. In some embodiments are provided methods of treating cancer in a patient, comprising administering to the patient a combination consisting essentially of entinostat, and an anti PD-1 or an anti-PD-L1 antibody, wherein the combination does not comprise any additional immunecheckpoint inhibitor. In some embodiments are provided methods of treating cancer in a patient, comprising administering to the patient a combination consisting essentially of entinostat, and an anti PD-1 or an anti-PD-L1 antibody, wherein the combination does not comprise an anti-CTLA4 inhibitor. In some embodiments are provided methods of treating cancer in a patient, comprising administering to the patient a combination consisting essentially of entinostat, and an anti PD-1 or an anti-PD-L1 antibody, wherein the combination does not comprise 5-azacytidine.

In some embodiments are provided methods of treating cancer in a patient, comprising administering to the patient a combination consisting essentially of entinostat and pembrolizumab. In some embodiments are provided methods of treating cancer in a patient, comprising administering to the patient a combination consisting essentially of entinostat and pembrolizumab, wherein said combination does not comprise an anti-CTLA4 inhibitor. In some embodiments are provided methods of treating cancer in a patient, comprising administering to the patient a combination consisting essentially of entinostat and pembrolizumab, wherein said combination does not comprise 5-azacytidine.

Methods of Selecting Patients for Combination Therapy

Provided herein in a further embodiment is a method of selecting patients for the combination therapy comprising administration of entinostat, and an anti PD-1 or an anti-PD-L1 antibody, wherein the selection is based on the level of PD-L1 expression in tumor.

Provided herein in a further embodiment is a method of selecting patients for the combination therapy comprising administration of entinostat, and an anti PD-1 or anti-PD-L1 antibody, wherein the selection is based on the tumor proportion score (TPS) for PD-L1 expression. Tumor proportion score is a measure of the percentage of cells in a tumor tissue sample that stains positiove for PD-L1 expression, as determined using immuhistochemistry. In some embodiments, the TPS is determined using a PD-L1 IHC 22C3 pharmDx kit.

In some embodiments, the method further comprises administering the combination therapy comprising entinostat, and an anti PD-1 or an anti-PD-L1 antibody to patients expressing elevated levels of PD-L1 in the tumor. In some embodiments, the method further comprises administering the combination therapy comprising entinostat, and an anti PD-1 or an anti-PD-L1 antibody to patients wherein the TPS is between 1% and 50%. In some embodiments, the method further comprises administering the combination therapy comprising entinostat, and an anti PD-1 or an anti-PD-L1 antibody to patients wherein the TPS is greater than or equal to 50%. In some embodiments, the tumor tissue sample wherein PD-L1 expression is measured is obtained from a non-small cell lung cancer patient. In some embodiments, the non-small cell lung cancer is a squamous cell carcinoma or a nonsquamous cell carcinoma. In some embodiments, the tumor sample wherein PD-L1 expression is measured is obtained from a melanoma patient. In some embodiments, the dosage of an anti PD-L1 or an anti-PD-L1 antibody used in the combination therapy is determined based on PD-L1 expression in tumor samples.

Methods of Evaluating Patients During Course of Treatment

Provided herein in a further embodiment is a method of treating cancer in a patient by administering a combination comprising entinostat, and an anti PD-1 or an anti-PD-L1 antibody, wherein the method further comprises steps for evaluation of biomarkers in biological sample obtained from the patient during the course of the combination therapy. In some embodiments the biological sample is a blood sample. In some embodiments, the biomarker is Lin (CD3, CD14, CD19, CD56) negative, HLA-DR-, CD33+ Myleoid derived suppresor cells (MDSC). In some embodiments, the biomarker is CD11b+CD14-CD33+ MDSC. In some embodiments, the biomarker is CD11b+; CD14−; CD33+; CD15+ Polymorphonuclear-MDSC. In some embodiments, the biomarker is CD11b+; CD14−; CD33+; CD15− monocytic MDSC. In some embodiments, the biomarker is CD14+; HLA-DR-/lo monocytic MDSC. In some embodiments, the biomarker is CD14+CD16+CD66b-HLA-DR+ monocytes, including subsets of classical CD14hiCD16, intermediate CD14hiCD16+, and non-classical CD14+CD16hi. In some embodiments, the biomarker is Lin-HLA-DR+CD303+ (BDCA2) plasmacytoid dendritic cells. In some embodiments, the biomarker is Lin-HLA-DR+CD1c+(BDCA1) myeloid dendritic cells. In some embodiments, the biomarker is Lin-HLA-DR+CD141+(BDCA3) dendritic cells. In some embodiments, the biomarker is CD11b+CD14−CD15+/CD66b+ neutrophil cells in high density fraction. In some embodiments, the biomarker is CD3+CD4+; CD3+CD8+ T-cells. In some embodiments, the biomarker is CD4+CD25+FoxP3+ regulatory T-cells. In some embodiments the biomarker is CD19+ B-cells.

In some embodiments administration of the combination therapy comprising entinostat and an anti-PD-1 or anti-PD-L1 therapy results in lowering of MDSC cells in peripheral blood sample. In some embodiments, the lowering of MDSC cells in peripheral blood sample during course of the treatment is correlated with a positive outcome of the combination therapy.

In some embodiments, the biomarker is protein lysine acetylation level in a tumor sample. In some embodiments, the biomarker is PD-L1 expression level in a tumor sample. In some embodiments, the biomarker is a tumor proportion score (TPS) for PD-L1 expression. In some embodiments, the TPS determined using a PD-L1 IHC 22C3 pharmDx kit. In some embodiments, the biomarker is e-cadherin level in a tumor sample. In some embodiments, the biomarker is $CD33^+$ and $S100A9^+$ myeloid derived suppressor cells (MDSC) in a tumor sample. In some embodiments, the biomarker is $CD33^+$ and $S100A9^+$ myeloid derived suppressor cells (MDSC) in peripheral blood sample. In some embodiments, the biomarker is $CD163^+$ or $CD68^+$ macrophages in a tumor sample. In some embodiments, the biomarker is $CD163^+$ or $CD68^+$ macrophages in peripheral blood sample. In some embodiments, the biomarker is neutrophil elastase in a tumor sample. In some embodiments, the biomarker is neutrophil elastase in serum sample. In some embodiments, the biomarker is dendritic cells (DC) expressing type II C-type lectin DC-SIGN (CD209). In some embodiments, the DC-SIGN (CD209) is detected in serum. In some embodiments, the DC-SIGN (CD209) is detected in a tumor sample. In some embodiments, the biomarker is CD4, CD8, Granzyme B and FoxP3 positive cells in a tumor samples.

Additional Therapy

Available additional treatments for lung cancer and melanoma that may be advantageously employed in combination with the therapies disclosed herein include, without limitation, radiation therapy, chemotherapy, antibody therapy, and tyrosine kinase inhibitors as adjuvant therapy.

Radiation therapy is a cancer treatment that uses high-energy x-rays or other types of radiation to kill cancer cells or keep them from growing. Chemotherapy is a cancer treatment that uses drugs to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the spinal column, an organ, or a body cavity such as the abdomen, the drugs mainly affect cancer cells in those areas (regional chemotherapy). The way the chemotherapy is given depends on the type and stage of the cancer being treated.

Different chemotherapeutic agents are known in the art for treating lung cancer. Cytoxic agents used for treating lung cancer include carboplatin (for example, Paraplatin®, Paraplat®), cisplatin (for example, Platinol®, Platinol-Aq®), crizotinib (for example Xalkori®), etoposide (for example Toposar®, VePesid®), etoposide Phosphate (for example Etopophos®), gemcitabine hydrochloride (for example Gemzar®), gemcitabine-cisplatin, methotrexate (for example Abitrexate®, Folex®, Folex Pfs®, Methotrexate Lpf®, Mexate®, Mexate-Aq®), paclitaxel (for example Taxol®), pemetrexed Disodium (for example Alimta®), and topotecan Hydrochloride (for example Hycamtin®)

Different agents are known in the art for treating melanoma, including aldesleukin (for example Proleukin®), dabrafenib (for example Tafinlar®), dacarbazine (for example DTIC-Dome®), recombinant Interferon Alfa-2b (for example Intron® A), Ipilimumab (for example Yervoy®), pembrolizumab (for example Keytruda®), Trametinib (for example Mekinist®), Nivolumab (for example Opdivo®), Peginterferon Alfa-2b (for example Pegintron®, Sylatron®), vemurafenib (for example Zelboraf®).

Monoclonal antibody therapy is a cancer treatment that uses antibodies made in the laboratory, from a single type of immune system cell. These antibodies can identify substances on cancer cells or normal substances that may help cancer cells grow. The antibodies attach to the substances and kill the cancer cells, block their growth, or keep them from spreading. Monoclonal antibodies are given by infusion. They may be used alone or to carry drugs, toxins, or radioactive material directly to cancer cells. Monoclonal antibodies are also used in combination with chemotherapy as adjuvant therapy.

Additional, illustrative, treatments that may be advantageously combined with the compositions and therapies disclosed herein may include, without limitation, administration of agents including, but not limited to lapatinib, alone or in combination with capecitabine, docetaxel, epirubicin, epothilone A, B or D, goserelin acetate, paclitaxel, pamidronate, bevacizumab, or trastuzumab.

In some embodiments, the additional therapy comprises chemotherapy comprising administering to the subject one or more of doxorubicin, cyclophosphamide, paclitaxel, lapatinib, capecitabine, trastuzumab, bevacizumab, gemcitabine, eribulin, or nab-paclitaxel.

Oral Formulations

Oral formulations containing the active pharmaceutical ingredients described herein may comprise any conventionally used oral forms, including: tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, syrups, buccal forms, and oral liquids. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. In some embodiments are surface modifying agents which include nonionic and anionic surface modifying agents. For example, surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

Oral Administration

As described herein, the combination therapy described herein can be given simultaneously or can be given in a staggered regimen, with entinostat being given at a different time during the course of chemotherapy than the EGFR inhibitor. This time differential may range from several minutes, hours, days, weeks, or longer between administrations of the two compounds. Therefore, the term combination does not necessarily mean administered at the same time or as a unitary dose, but that each of the components are administered during a desired treatment period. The agents may also be administered by different routes. As is typical for chemotherapeutic regimens, a course of chemotherapy may be repeated several weeks later, and may follow the same timeframe for administration of the two compounds, or may be modified based on patient response.

In other embodiments, the pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

In further embodiments, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

In other embodiments, the pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

In other embodiments, the pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

In further embodiments, the pharmaceutical compositions provided herein may be co-formulated with other active ingredients which do not impair the desired therapeutic action, or with substances that supplement the desired action.

EXAMPLES

Example 1

A Phase 1B/2, open-label, dose escalation study of entinostat in combination with pembrozulimab in patients with non-small cell lung cancer, with expansion cohorts in patients with non-small cell lung cancer and melanoma.

The combination of entinostat with pembrozulimab improves the response to PD-1 blocking antibody treatment and results in improved response rate compared to administration of either agent alone, in patients with non-small cell lung cancer and melanoma, with an acceptable safety profile.

Primary Objective:
Number of Participants taking 3 mg entinostat weekly with Adverse events as a measure of Safety and Tolerability.
Number of Participants taking 5 mg entinostat weekly with Adverse Events as a measure of Safety and Tolerability.
Number of Participants taking 10 mg entinostat every other week with Adverse events as a Measure of Safety and Tolerability.

Phase 1b (Dose Escalation/Confirmation Cohorts):
To determine the dose-limiting toxicities (DLT) and maximum tolerated dose (MTD) or recommended Phase 2 dose (RP2D) of entinostat (SNDX-275) given in combination with pembrolizumab.
Phase 2 (Expansion Cohorts): To evaluate the preliminary efficacy of entinostat at the RP2D in combination with pembrolizumab in patients with melanoma and NSCLC, as determined by overall response rate (ORR), per the Immune-related Response Evaluation Criteria in Solid Tumors (irRECIST) in each cohort evaluated.

Secondary Objectives:
Efficacy: To evaluate the efficacy of entinostat in combination with pembrolizumab in patients with melanoma and NSCLC, as determined by secondary measures of efficacy based on both irRECIST and RECIST 1.1, including:
Clinical benefit rate (CBR) (i.e., complete response [CR]+ partial response [PR]+stable disease [SD]) at 6 months.
Progression-free survival (PFS) status at 6 months.
PFS
Overall survival (OS)
In patients who experience a response to treatment (i.e., CR or PR):
Duration of response (DOR)
Time to response (TTR)
Safety: To evaluate safety and the tolerability of entinostat in combination with pembrolizumab, as measured by clinical adverse events (AEs), laboratory parameters, and electrocardiograms (ECGs). Study Design
Patients enrolled for the combination therapy described herein receive two weeks of monotherapy with entinostat only. After completion of the two week monotherapy, patients enter a treatment cycle for the combination therapy period. Each treatment cycle lasts for 21 days, during which the patients receive entinostat in combination with pembrolizumab. Phase 2 (Expansion phase)

Primary Objective
Evaluate the preliminary efficiency of entinostat at the RP2D in combination with pembrozulimab in patients with melanoma and NSCLC, as determined primarily by overall response rate (ORR).

Secondary Objectives
The secondary objectives are same as those listed for Phase 1B.
Primary Endpoints
Overall Response Rate (ORR)
Clinical Benefit Rate (CBR)
Duration of Response (DOR)
Time to response (TTR)
Progression Free Survival (PFS) status at 6 months
Progression Free Survival (PFS)
Overall Survival (OS)
Secondary Endpoints
Safety: AEs, clinical laboratory parameters, and ECGs.

Pharmacodynamics: Protein acetylation in peripheral blood mononuclear cells (PBMCs)
Exploratory:
Changes in expression of checkpoint inhibitors (PD-1/PD-L1) in tumor biopsies pre- and post-therapy
Ratio of effector T cells:regulatory T cells in tumor biopsies pre- and post-therapy (immunohistochemistry)
Changes in number of MDSCs in peripheral blood and tumor biopsies
Changes in protein lysine acetylation in peripheral blood cells and tumor biopsies pre- and post-therapy
PK profiles of entinostat and pembrolizumab
Inflammatory T cell signature changes in blood and tumor biopsies pre- and post-therapy
Gene expression profiling pre and post biopsy
Changes in other immune markers of regulatory mechanisms and other assessments of collected/stored samples of biological specimens
Immunogenicity of pembrolizumab in combination with entinostat
Exposure-safety response of entinostat when given in combination with pembrolizumab
Blood levels of the following exemplary markers of immunologic efficiency are evaluated:
Myeloid derived suppresor cells (MDSC): Lin (CD3, CD14, CD19, CD56) negative; HLA-DR$^-$; CD33$^+$
MDSC: CD11b$^+$CD14$^-$CD33$^+$
Polymorphonuclear-MDSC (PMN-MDSC): CD11b$^+$; CD14$^-$; CD33$^+$; CD15$^+$
Monocytic (M-MDSC): CD11b$^+$; CD14$^-$; CD33$^+$; CD15$^-$
M-MDSC: CD14$^+$; HLA-DR$^{-/lo}$
Monocytes: CD14$^+$CD16$^+$CD66b$^-$HLA-DR$^+$, including subsets of classical CD14$^{hi}$CD16$^+$, intermediate CD14$^{hi}$CD16$^+$, and non-classical CD14$^+$CD16$^{hi}$
Dendritic cells: Lin$^-$HLA$^-$DR$^+$CD303$^+$ (BDCA2) plasmacytoid; Lin$^-$HLADR$^+$CD1c$^+$ (BDCA1) myeloid; Lin$^-$HLA$^-$DR$^+$CD141$^+$ (BDCA3)
Neutrophils: CD11b$^+$CD14$^-$CD15$^+$/CD66b$^+$ cells in high density fraction
T cells: CD3$^+$CD4$^+$; CD3$^+$CD8$^+$; Regulatory T cells: CD4$^+$CD25$^+$FoxP3$^+$
B cells: CD19
Cellular functions are assessed by measuring the levels of interleukin-2 (IL-2), interferon-gamma (IFN-γ), and granulocyte macrophage-colony stimulating factor (GM-CSF) in mononuclear cells stimulated with CD3/CD28, ConA, and tetanus toxoid.
Cell proliferation is evaluated by $^3$H-thymidine uptake assay.
The tumor biopsy tissues collected during various stages of treatment with combination therapies described herein, are evaluated for:
Acetylation
PD-L1 expression
e-Cadherin levels
MDSC: CD33$^+$S100A9$^+$
Macrophages CD163$^+$ or CD68$^+$ cells
Neutrophils—Neutrophil elastase cells
Dendritic cells—DC-SIGN (CD209)
CD4, CD8, Granzyme B and FoxP3 positive cells, as appropriate, if the MDSC level in tissue is decreased
Study Design
The expansion phase begins after DLT, MTD, and RP2D are identified during the dose escalation phase. In this phase entinostat is evaluated using the RP2D identified in the Dose escalation phase. The initial patients will receive entinostat at a starting dose of 3 mg on D1, D8, and D15 along with pembrolizumab 200 mg via intravenous (IV) infusion on D1 of a 21-day cycle.

The following patient cohorts may be selected for participating in this phase:
- Cohort 1: NSCLC, with squamous cell or adenocarcinoma histology who have not been treated with a PD-1 or PDL-1 blocking antibody
- Cohort 2: Patients with NSCLC (any histology) who have previously been treated with and progressed on either a PD-1 or PD-L1-blocking antibody
- Cohort 3: Patients with melanoma who have previously been treated with and progressed on either a PD-1 or PD-L1-blocking antibody.

Entinostat Monotherapy Immune Correlate (EMIC) Cohort:

Up to 20 NSCLC patients Stage 2 of Cohort 1 will be randomly assigned to participate. Sample Size Dose Escalation/Confirmation Phase Three to 6 patients will be enrolled in each dose cohort based on a standard Phase 1 dose escalation scheme. Each patient will participate in only 1 dose cohort. The total number of patients to be enrolled in the Dose Escalation/Confirmation Phase is dependent upon the observed safety profile, which will determine the number of patients per dose cohort, as well as the number of dose escalations required to achieve the MTD or RP2D. A total of 9 additional patients will be enrolled at the potential RP2D in the Dose Confirmation Cohort to obtain additional AE, immune correlate, and anti-tumor activity data on entinostat at the MTD or other dose recommended for further investigation in Phase 2 (i.e., RP2D) in combination.

Expansion Phase

Up to 136 patients are planned to be enrolled among the 3 cohorts. Patients will be enrolled in each cohort according to a single-arm study design with ORR as the primary endpoint. The Expansion Phase will be carried out in 2 stages so that enrollment for 1 or more of the cohorts evaluated can terminate early in the event the antitumor activity of the combination regimen is not sufficient. The decision to terminate or continue enrollment for each cohort will be made independently of the other cohorts. The protocol may be amended to allow for enrollment of additional or different cohorts based on emerging data during study conduct The combination therapy with entinostat and pembrolizumab is evaluated in each of the four cohotors following the criterion described below:

Inclusion Criteria

Patients with NSCLC:
1. Has histologically- or pathologically-confirmed recurrent/metastatic NSCLC.
2. If has adenocarcinoma, required to have previously been tested for anaplastic lymphoma kinase (ALK) rearrangements and epidermal growth factor receptor (EGFR) mutations, with results available for collection in this study, and, if positive, has been treated with prior EGFR or ALK therapy.
3. Received at least 1 chemotherapeutic regimen in the advanced/metastatic setting Patients with Melanoma:
1. Has a histologically- or cytologically-confirmed diagnosis of unresectable or metastatic melanoma and experienced PD following a PD-1 or PD-L1-blocking antibody and, if BRAF V600 mutation-positive, a BRAF inhibitor.

Patients in Expansion Phase, Cohorts 2 and 3
2. Previously treated with a PD-1/PD-L1-blocking antibody and experienced PD during such treatment.

Patients in Expansion Phase, Cohorts 2 (NSCLC) and 3 (Melanoma)
1. Previously treated with a PD-1/PD-L1-blocking antibody (i.e., pembrolizumab, nivolumab, MEDI4736, or GNE PD-L1 [MPDL3280A]) and experienced documented, unequivocal progressive disease by RECIST 1.1 or clinically during or after such treatment.

All Patients:
1. Aged 18 years or older on the day written informed consent is given.
2. If has brain metastases, must have stable neurologic status following local therapy for at least 4 weeks without the use of steroids or on stable or decreasing dose of ≤10 mg daily prednisone (or equivalent), and must be without neurologic dysfunction that would confound the evaluation of neurologic and other AEs.
3. Evidence of locally recurrent or metastatic disease based on imaging studies within 28 days before the first study drug dose:
4. At least 1 measurable lesion ≥20 mm by conventional techniques or ≥10 mm by spiral CT scan or MRI, with the last imaging performed within 28 days before the first study drug dose. If there is only 1 measurable lesion and it is located in previously irradiated field, it must have demonstrated progression according to RECIST, version 1.1.
5. If receiving radiation therapy, has a 2-week washout period following completion of the treatment prior to receiving the first study drug dose and continues to have at least 1 measurable lesion, per above criterion.
6. ECOG performance status of 0 or 1.
7. Has acceptable, applicable laboratory parameters.
8. Female subjects must not be pregnant.
9. If male, agrees to use an adequate method of contraception
10. Experienced resolution of toxic effect(s) of the most recent prior chemotherapy to Grade 1 or less (except alopecia). If patient underwent major surgery or radiation therapy of >30 Gy, they must have recovered from the toxicity and/or complications from the intervention.
11. Willing to have fresh tumor samples collected during screening and at other time points designated as mandatory, per the Schedule of Study Assessments.
12. Able to understand and give written informed consent and comply with study procedures.

Exclusion Criteria

Patients meeting any of the following criteria are not considered eligible to participate in the study:
1. Diagnosis of immunodeficiency or receiving systemic steroid therapy or any other form of immunosuppressive therapy within 7 days prior to the first dose of study drug. The use of physiologic doses of corticosteroids may be approved after consultation with the Sponsor.
2. Active autoimmune disease that has required systemic treatment in past 2 years (i.e., with disease modifying agents, corticosteroids, or immunosuppressive drugs). Replacement therapy (e.g., thyroxine, insulin, or physiologic corticosteroid replacement therapy for adrenal or pituitary insufficiency) is not considered a form of systemic treatment.
3. History of interstitial lung disease (ILD).
4. Allergy to benzamide or inactive components of entinostat.
5. History of allergies to any active or inactive ingredients of pembrolizumab.

6. History or current evidence of any condition, therapy, or laboratory abnormality that might confound the results of the study, interfere with the patient's participation for the full duration of the study, or is not in the best interest of the patient to participate, in the opinion of the treating Investigator, including, but not limited to:
7. Myocardial infarction or arterial thromboembolic events within 6 months prior to baseline or severe or unstable angina, New York Heart Association (NYHA) Class III or IV disease, or a QTc interval>470 msec.
8. Uncontrolled heart failure or hypertension, uncontrolled diabetes mellitus, or uncontrolled systemic infection.
9. Another known additional malignancy that is progressing or requires active treatment (excluding adequately treated basal cell carcinoma or cervical intraepithelial neoplasia [CIN]/cervical carcinoma in situ or melanoma in situ). Prior history of other cancer is allowed, as long as there is no active disease within the prior 5 years.
10. Evidence of pneumonitis or history of pneumonitis.
11. Active infection requiring systemic therapy.
12. Known active central nervous system (CNS) metastases and/or carcinomatous meningitis.
13. Note: Patients with previously treated brain metastases may participate provided they are stable (without evidence of progression by imaging [using the identical imaging modality for each assessment, either MRI or CT scan] for at least 4 weeks prior to the first dose of study drug and any neurologic symptoms have returned to baseline), have no evidence of new or enlarging brain metastases, and are not using steroids for at least 2 weeks prior to the first dose of study drug or are on stable or decreasing dose of ≤10 mg daily prednisone (or equivalent). This exception does not include carcinomatous meningitis which is excluded regardless of clinical stability.
14. Known psychiatric or substance abuse disorders that would interfere with cooperation with the requirements of the study.
15. Currently participating and receiving study therapy or has participated in a study of an investigational agent and received study therapy or used an investigational device within 4 weeks of the first dose of treatment.
16. Received a live vaccine within 30 days of the first dose of treatment.
17. Prior anti-cancer monoclonal antibody (mAb) within 4 weeks prior to baseline or who has not recovered (i.e., Grade 1 or at baseline) from AEs due to agents administered more than 4 weeks earlier.
18. Prior chemotherapy, targeted small molecule therapy, or radiation therapy within 2 weeks prior to study baseline or who has not recovered (i.e., ≤Grade 1 or at baseline) from AEs due to a previously administered agent. Note: Patients with ≤Grade 2 neuropathy or ≤Grade 2 alopecia are an exception to this criterion and may qualify for the study. Note: If patient underwent major surgery, they must have recovered adequately from the toxicity and/or complications from the intervention prior to starting therapy.
19. Received transfusion of blood products (including platelets or red blood cells) or administration of colony stimulating factors (including granulocyte-colony stimulating factor [G-CSF], granulocyte macrophage- colony stimulating factor [GM-CSF], or recombinant erythropoietin) within 4 weeks prior to the first dose of treatment.
20. Currently receiving treatment with any other agent listed on the prohibited medication list such as valproic acid, or other systemic cancer agents within 14 days of the first dose of treatment.
21. If female, is pregnant, breastfeeding, or expecting to conceive, or if male, expect to father children within the projected duration of the study, starting with the screening visit through 120 days after the last dose of study drug.
22. Known history of human immunodeficiency virus (HIV) (HIV 1/2 antibodies).
23. Known active hepatitis B (e.g., hepatitis B surface antigen-reactive) or hepatitis C (e.g., hepatitis C virus ribonucleic acid [qualitative]).
24. Is or has an immediate family member (e.g., spouse, parent/legal guardian, sibling, or child) who is investigational site or sponsor staff directly involved with this study, unless prospective Institutional Review Board (IRB)/Ethics Committee (EC) approval (by chair or designee) is given allowing exception to this criterion for a specific patient.

Example 2

ENCORE 601: Phase 1b/2 study designed to evaluate entinostat in combination with pembrolizumab in patients with advanced NSCLC or melanoma.

Methods

Patients with Stage III/IV NSCLC previously treated with platinum-based chemotherapy were enrolled in the 3+3 dose escalation phase. Entinostat administered orally at 3 mg once a week (qW) or at 5 mg qW in combination with a fixed dose of pembrolizumab at 200 mg every three weeks (q3W), delivered via intravenous route, in 21-day cycles were explored to determine the safety and MTD or RP2D. Evaluation markers correlated to treatment progress included included tumor PD-L1 expression and change in MDSCs and regulatory T cells in peripheral blood samples.

Results

Nine patients were enrolled (six of them were administered 3 mg entinostat and 3 were administered 5 mg qW) with the pembrolizumab combination as indicated above. No DLTs have been observed in 8 of 9 patients. One patient, treated with 3 mg entibostat, developed grade 3 elevated alkaline phosphatase and bilirubin during cycle 2, which were considered manifestations of immune-mediated hepatitis. This was successfully and rapidly managed by holding study drugs and administering systemic corticosteroids. In 2 of 3 patients with paired peripheral blood samples, decreases in MDSCs from baseline were observed. Stable disease was observed in 3 of 6 patients evaluated.

CONCLUSION

Entinostat combined with pembrolizumab appeared to be well tolerated and had immunomodulatory activity as indicated by the lowering of MDSCs from baseline upon administration of the combination.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating melanoma or non-small cell lung cancer in a patient in need thereof comprising administering to the patient a combination of therapeutic agents to said patient, wherein:
    the therapeutic agents consist essentially of entinostat and pembrolizumab,
    the patient previously received a PD-1-blocking antibody or PD-L1-blocking antibody, and
    the patient progressed on prior therapy with a PD-1-blocking antibody or PD-L1-blocking antibody.

2. The method of claim 1, wherein the patient progressed on prior therapy with a PD-1-blocking antibody.

3. The method of claim 1, wherein patient progressed on prior therapy with pembrolizumab.

4. The method of claim 1, wherein entinostat is administered orally.

5. The method of claim 1, wherein entinostat is administered once per week.

6. The method of claim 1, wherein the pembrolizumab is administered intravenously.

7. The method of claim 1, wherein the pembrolizumab is administered every two weeks.

8. The method of claim 1, wherein the initial doses of the combination are administered simultaneously.

9. The method of claim 1, wherein the cancer is melanoma.

10. The method of claim 9, wherein the melanoma is unresectable or metastatic melanoma.

11. The method of claim 1, wherein the cancer is non-small cell lung cancer.

12. The method of claim 11, wherein the non-small cell lung cancer is selected from adenocarcinoma, squamous cell carcinoma, and large cell carcinoma.

13. A method for treating melanoma or non-small cell lung cancer in a patient in need thereof comprising administering to the patient a combination of therapeutic agents to said patient, wherein:
    the therapeutic agents consist of entinostat and pembrolizumab,
    the patient previously received a PD-1-blocking antibody or PD-L1-blocking antibody, and
    the patient progressed on prior therapy with a PD-1-blocking antibody or PD-L1-blocking antibody.

14. The method of claim 13, wherein the patient progressed on prior therapy with a PD-1-blocking antibody.

15. The method of claim 13, wherein patient progressed on prior therapy with pembrolizumab.

16. The method of claim 13, wherein entinostat is administered orally.

17. The method of claim 13, wherein entinostat is administered once per week.

18. The method of claim 13, wherein the pembrolizumab is administered intravenously.

19. The method of claim 13, wherein the pembrolizumab is administered every two weeks.

20. The method of claim 13, wherein the initial doses of the combination are administered simultaneously.

21. The method of claim 13, wherein the cancer is melanoma.

22. The method of claim 21, wherein the melanoma is unresectable or metastatic melanoma.

23. The method of claim 13, wherein the cancer is non-small cell lung cancer.

24. The method of claim 23, wherein the non-small cell lung cancer is selected from adenocarcinoma, squamous cell carcinoma, and large cell carcinoma.

* * * * *